United States Patent

Silver

[11] 4,248,228
[45] Feb. 3, 1981

[54] DISPOSABLE ENEMA SYRINGE FOR ONE HAND USE

[76] Inventor: Jules Silver, Rte. 32, North Franklin, Conn. 06254

[21] Appl. No.: 86,433

[22] Filed: Oct. 19, 1979

Related U.S. Application Data

[63] Continuation of Ser. No. 885,020, Mar. 9, 1978, abandoned.

[51] Int. Cl.³ .............................................. A61M 1/00
[52] U.S. Cl. ..................................... 128/234; 128/261
[58] Field of Search .............. 128/234, 232, 239, 260, 128/261

[56] References Cited

U.S. PATENT DOCUMENTS

| | | | |
|---|---|---|---|
| 2,862,496 | 12/1958 | Hassler et al. | 128/261 |
| 2,902,035 | 9/1959 | Hartley | 128/234 |
| 3,882,866 | 5/1975 | Zackheim | 128/261 |
| 4,127,126 | 11/1978 | Schunk | 128/234 |

Primary Examiner—John D. Yasko
Attorney, Agent, or Firm—Murray & Whisenhunt

[57] ABSTRACT

There is provided a disposable enema syringe for self-application and/or one hand use wherein the syringe is of the type having a barrel with a transversely extending flange at least partially disposed about the open end thereof, a movable piston disposed within the bore of the barrel and a plunger having one end connected to the piston and the other end extending out of the bore and terminating in a digit receiving pressure pad. The pressure pad is at a distance from the flange such that the syringe may be controllably grasped by one hand between the thumb and a finger around the barrel and next to the flange and the index or second finger on the pressure pad. The syringe has a soft and flexible cannula which is sufficiently long that it may be inserted into the rectum and past the sphincter muscles and sufficiently short that it may be inserted into the rectum with only one hand. Thus, the cannula may be inserted into the rectum and the enema fluid injected from the syringe into the rectum with the use of only one hand.

8 Claims, 4 Drawing Figures

DISPOSABLE ENEMA SYRINGE FOR ONE HAND USE

This is a continuation of application Ser. No. 885,020 filed Mar. 8, 1978 now abandoned.

The present invention relates to an enema syringe for easy, convenient and aesthetic administration unassisted or assisted by the user. More particularly, the invention relates to such syringe wherein operation of the syringe, i.e., expelling its contents, may be accomplished with one hand, and without direct contact of the hand with the anal opening.

BACKGROUND OF THE INVENTION

The injection of a liquid into the colon by way of the anus is commonly referred to as an enema and is used in a variety of therapeutic and pre-surgical procedures. However, due to the nature of the enema, there is a strong resistance by patients to the use of an enema, even though the therapeutic and pre-surgical procedures are often well-advised. A primary cause for this resistance to the enema is the difficulty and inconvenience of self-application of the enema and the corresponding often required assistance for application of the enema. In addition, there is substantial resistance to the use of an enema which is applied by re-usable devices, since these devices not only suffer from the psychological impact of prior use but require cleaning after use.

To mitigate these difficulties associated with enemas, the art has proposed a number of disposable enema devices, which avoid the above-noted psychological impact of prior use and the requirement for subsequent cleaning. Some of the proposed devices, in addition to being of a disposable nature, are constructions which can be referred to as self-application devices, but these devices are either difficult to operate in a self-application mode or are inconvenient for self-application due to special considerations which must be observed in that self-application. These devices also involve direct contact or close proximity to the anal opening during administration which increases psychological user resistance.

In this latter regard, gravity feed devices have been proposed wherein the devices are composed of, essentially, a disposable plastic bag reservoir for the enema fluid, discharge tubing and a nozzle at the end of the discharge tubing. Various valving arrangements have been proposed for expelling the enema fluid from the reservoir through the tubing and through the nozzle into the rectum. Variations of these devices include provision for manually squeezing the reservoirs to further force enema fluid from the reservoir through the tubing and nozzle. Representative of this art is U.S. Pat. No. 2,784,716. As can be appreciated, however, these devices are quite bulky and difficult to handle. The reservoir must either be supported by some independent mechanical means or it must be held in one hand while the tip of the device is inserted into the rectum. Insertion becomes difficult if the reservoir is held by one hand since the other hand of the user cannot conveniently both separate the buttocks and insert the tip into the rectum. Special lubricated tips, shapes thereof and the like have been proposed to mitigate this problem, but these improvements have proven somewhat unsatisfactory.

Another approach in the art is to provide a small reservoir to which the insertion nozzle is directly attached. These devices are relatively large and difficult to manipulate, especially by one hand.

In U.S. Pat. No. 3,882,866, background of the above nature and prior U.S. patents directed to the art are discussed in some detail, the disclosure of which patent is incorporated herein by reference. That patent goes on to propose a disposable enema device which is a combination of a piston/barrel-type syringe and a lubricated cannula attached thereto. The enema fluid is dispelled into the rectum through the cannula by digitally forcing the piston into the barrel of the syringe by way of a plunger. A major feature of that invention is using the removed rigid cannula cover as the plunger for the piston whereby a more compact unit may be provided. Self-application or use of the syringe with only one hand is not specified in that patent.

It would be, of course, most valuable in the art to provide a syringe of the nature disclosed in U.S. Pat. No. 3,882,866, but which is so arranged that it is more amenable to self-application and, preferably, can be operated by the user with only one hand, thus leaving the other hand available for more comfortable insertion of the cannula. The present invention provides a syringe of that nature.

BRIEF SUMMARY OF THE INVENTION

The present invention is based on three primary features. The first feature is that since effective volumes of enema fluid can be as little as 8-10 ml, particularly, when the more modern enema fluids are utilized, an efficiently used syringe may have a correspondingly small volume, i.e., no substantial excess volume is necessary. A second major feature of the invention is that a syringe of the foregoing nature can be comfortably inserted into the rectum when the cannula has a relatively critical combination of flexibility, softness and length. With the requisite flexibility, the angle of insertion of the cannula by the user into the anal opening is not so critical for comfort as is the angle with a relatively rigid cannula. With a soft material, application by the user with one hand may still be comfortable since the likelihood of abrading or scratching the sensitive tissue around the anal opening is significantly decreased. With the combination of flexibility and softness, the length of the cannula becomes critical, since the cannula must be long enough for full insertion past the sphincter muscles but must be short enough that the flexible cannula can still be controllably inserted past the sphincter muscles, especially with only one hand. As another feature of the invention the syringe must be of a size such that the plunger of the syringe may be operated from its fully extended position to its fully depressed position with only one hand. Other subsidiary features of the invention will be more apparent from the detailed disclosure.

Thus, there is provided a disposable enema syringe for self-application and for one hand use which comprises a barrel with a bore therein and the barrel having an open end with a traversely extending flange at least partially disposed about the open end and the barrel having a discharge end with a discharge orifice therein. A movable piston is disposed within the bore, whereby an enema fluid receiving cavity in the bore is defined by the space between the piston and the discharge end of the barrel. A plunger is provided having one end operably connected to the piston and the other end extending out of the bore and terminating in a digit receiving pressure pad. That pressure pad is at a distance from the flange which is at least substantially equal to the distance of the cavity between the piston and the discharge end of the barrel. Further the distance from the flange to the pressure pad is such that the syringe may be controllably grasped by one hand between the thumb and a finger around the barrel and next to the flange, and the index or second finger on the said pressure pad. Of course, the syringe may be held in the conventional manner with the thumb on the pressure pad and the barrel held by fingers, and the specification and claims should be so understood. The syringe must, however, be capable of being held in the foregoing manner. A soft and flexible cannula has an end in fluid communication with the discharge orifice, and the other end has a cannula orifice. The cannula is sufficiently long that it may be inserted into the rectum and past the sphincter muscles and yet sufficiently short that it may be inserted into the rectum with only one hand, especially by the user. Therefore, the cannula may be inserted into the rectum, and the enema fluid injected from the syringe into the rectum with the use of only one hand. By this arrangement, the other hand, especially of the user, is free for more comfortable insertion of the cannula. In addition, the syringe is of such small size that it may be self-applied by the user when in any recommended conventional positions. Thus, the present enema can be unassistedly used in total privacy and with very convenient use of a conventional position. This constitutes a substantial improvement in the art.

DETAILED DESCRIPTION OF THE DRAWINGS

DETAILED DESCRIPTION OF THE PREFERRED INVENTION

Figure 1:
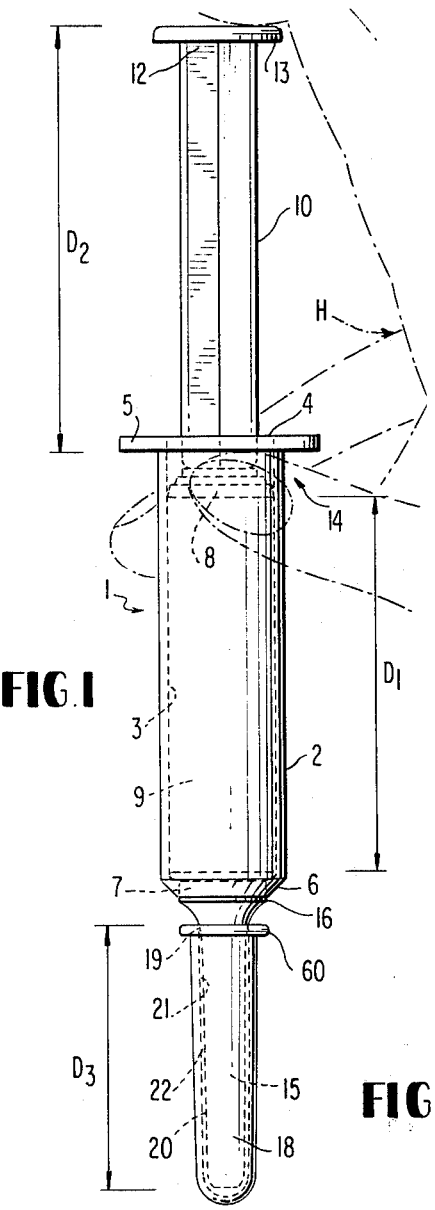
FIG. 1 is a side view of the syringe as prepared in manufacture.

As can be seen from FIG. 1, the syringe, generally 1, consists of a barrel 2 having a bore 3 with an open end 4 and transversely extending flange 5 about the open end. The barrel has a discharge end 6 with a discharge orifice 7. A movable piston 8 is disposed within bore 3 whereby an enema fluid receiving cavity 9 in the bore 3 is defined by the space between the piston 8 and the discharge end 6 of the barrel. A plunger 10 has one end 11 operably connected to piston 8 and the other end 12 extending out of bore 3 and terminating in a digit receivable pressure pad 13. In the fully extended position of plunger 10, e.g., with cavity 9 containing the enema fluid, the pressure pad 13 is at a distance from flange 5 which is at least substantially equal to the distance $D_1$ of the cavity between the piston and discharge end. This of course allows the plunger to cause the piston to traverse essentially the entire cavity 9 and expel the enema fluid therefrom.

In order to provide operation of the syringe by one hand of the user, it is critical that the distance $D_2$ from flange 5 to pressure pad 13 be such that the syringe may be controllably grasped by one hand of the user with the fingers of the user around the barrel and next to the flange, generally in area 14, and with the user's second finger on pressure pad 13. The general phantom outline of the hand in such position is shown as 15. With the syringe being graspable in this position, the user may comfortably insert the cannula 15 into the rectum and expel the contents from cavity 9 with only one hand operating the syringe.

Cannula 15 is a soft and flexible cannula with one end 16 being in fluid communication with the discharge orifice 7 of the barrel and the other end thereof having a cannula orifice 17. The cannula is sufficiently long, i.e., having a distance $D_3$ that it may be inserted into the rectum and past the sphincter muscles, but is sufficiently short that it may be controllably inserted into the rectum, especially by the user, with use of only one hand. For this purpose, the cannula is preferably constructed of a material which is substantially more soft and flexible than the material from which the barrel is constructed. As shown in FIG. 1, and more specifically in FIG. 3, the cannula is preferably a separate piece of softer and more flexible material, which is inserted into barrel 2 of the syringe to provide the fluid communication and also to provide a fluid seal between the cannula and the barrel. However, it should be understood that the discharge end of the barrel, and indeed the entire barrel, and the cannula may be constructed of the same material and together form a monolithic unit. However, in this embodiment, it will be necessary to provide a combination of material and wall thicknesses of the cannula such that the soft and flexible cannula, as defined above, still results. This arrangement does have the advantage in that there is no concern for a seal between the cannula and the barrel. As noted above, when the cannula is produced of a separate material and placed in the discharge end of the barrel, the construction must provide that the discharge end forms a seal with the cannula.

During shipment and prior to use of the syringe, the cannula will be protected by removable cannula cap 18, which extends at least over the cannula orifice. This will, of course, prevent leakage of the enema fluid from cavity 9 out of cannula orifice 17. However, both for sanitary purposes and aesthetic purposes, preferably, cannula cap 18 extends at least over the portion of the cannula which will be inserted into the rectum of the user when used. More preferably, the cap will extend over essentially the entire cannula.

For ease of insertion of the cannula into the anal opening and past the sphincter muscles, it is preferred that the cannula have a decreasing taper from the end thereof next to the discharge orifice of the barrel (immediately below the seal 16) to the cannula orifice 17. Further, in this embodiment, it is preferred that the cannula cap 18 have a corresponding taper but which taper terminates at a distance ($D_3$) where the cannula cap will form a friction mating, i.e., in the area 19, between the inside surface of the cannula cap and the outside surface of the cannula. Preferably, this friction mating is at a portion of the cannula which will not be inserted into the rectum of the user when the syringe is used. Therefore, the entire portion of the cannula inserted into the rectum will have been protected by the removed cannula cap. This embodiment also allows that the tapers form an annulus between the cannula and the cannula cap. This annulus allows enema fluid from cavity 9 to flow into the annulus and provide a self-lubricated cannula, particularly, with modern enema fluids which have an inherent lubricity. These tapers can best be seen in FIG. 2 where the taper 20 of the cannula outside surface corresponds to the taper 21 of the cannula cap inside surface in such a manner as to provide an annulus 22 (as shown in FIG. 1).

If desired the cannula cap may be removed and placed on the piston to function as the plunger, as disclosed in the above-identified U.S. Pat. No. 3,882,866.

Figure 2:
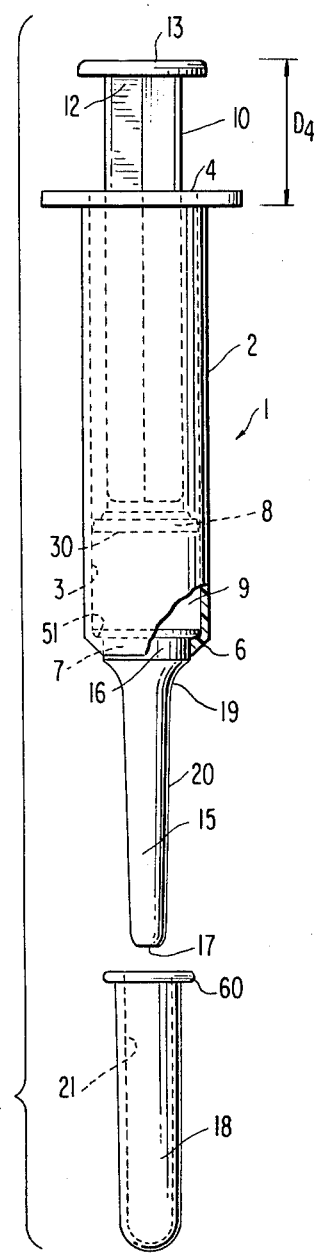
FIG. 2 is a side view of the syringe of FIG. 1 showing the cannula cap removed and the plunger being depressed as would be the configuration after expelling at least some of the contents of the syringe.

Note in FIG. 2 that plunger 10 has been depressed into barrel 2 which would cause a corresponding expelling of enema fluid from cavity 9. In this regard, the plunger may be arranged so that it expels essentially the entire volume of enema fluid when the plunger has been depressed to the position shown in FIG. 2, i.e., depressed to a distance $D_4$ from flange 5, but it is preferred that the plunger be arranged such that its length when fully depressed is at flange 5 or only slightly thereabove.

Figure 3:
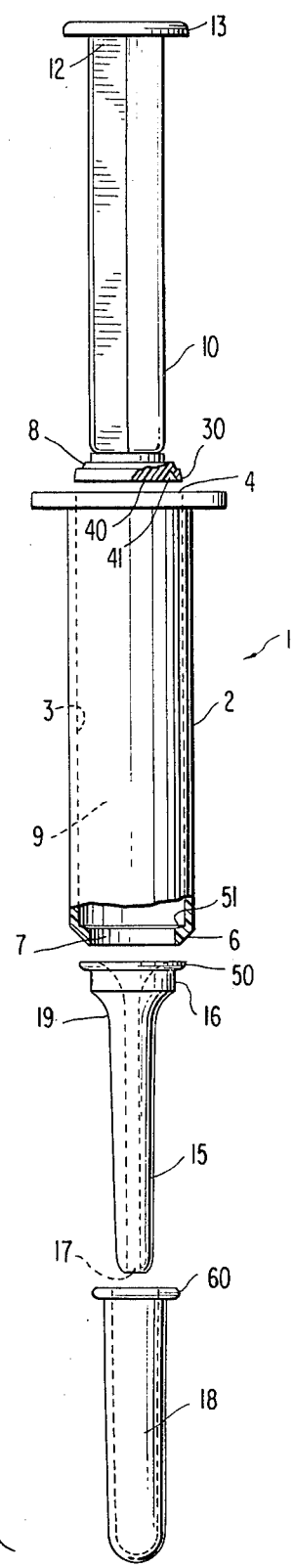
FIG. 3 is an exploded side view of the syringe, including the cannula cap.

FIG. 3 shows an exploded view of the syringe. Pressure pad 13 may be a digit plate or simply a flattened extension of plunger 10. The particular shape of pressure pad 13 is not critical, and need only be a convenient surface by which the plunger may be digitally operated.

The plunger may be a solid rod, but more conveniently, is a structural section such as a tube, triangle, angle or intersecting sections, as shown in FIGS. 1 through 3. The intersecting sections, of course, form a right-angle "X" in cross-sectional view (not shown). The piston 8, preferably has a tapered skirt 30 to create an effective seal between that skirt and the inside wall of bore 3. The piston is attached to plunger 10 in any convenient manner, but when the piston and plunger are made of a moldable material, such as plastic, pressure pad 13, plunger 10 and piston 8, along with skirt 30, may be a monolithic plastic material. Irrespective, the piston effects a seal with the bore by any convenient means, such as skirt 30 (see FIG. 4) which is flexibly bendable and toward support section 40 by virtue of moving into annular space 41. Other arrangements, as desired, may be used.

Figure 4:
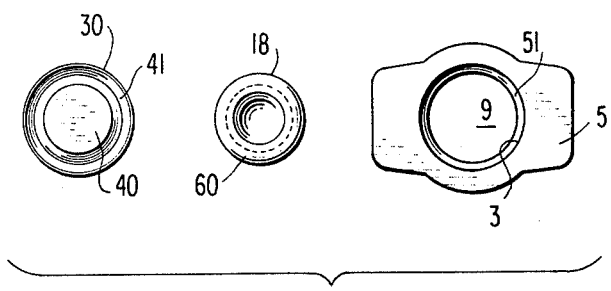
FIG. 4 is an end view of, respectively, the piston, cannula cap and the open end of the syringe barrel having extending flanges.

Flange 5 may be a simple finger flange, as more specifically shown in FIG. 4, or it may be a circular flange or anything in between, as desired. It is only necessary to provide some mechanical surface for supporting the thumb and finger so that the index or second finger may depress plunger 10 via action or force on pressure pad 13.

Cannula 15 is conveniently sealed to barrel 2 by seal 16. That seal consists of a flange 50 (see FIG. 3) which cooperates with flange 51 in the discharge end 6 of barrel 2. Since the material of separately produced cannula 15 is the soft and flexible type, that arrangement will inherently provide a seal between discharge end 6 and cannula 15.

Cannula cap 18 is also preferably of a relatively soft and yieldable material so that the cap may form the friction mating with the cannula at area 19 without scoring or otherwise roughening the cannula. However, instead of friction mating between the cannula and cannula cap, other locking means such as a rib and identation, which is well-known in the art, may be used. Other similar mechanical lockings may be used if desired. However, it is preferred that the cannula cap have a lip 60 (see particularly FIG. 4) so that it may be easily removed, when desired, from cannula 15. At least, the lip should be yieldable so as to provide an effective seal between cannula 15 and the cannula cap, particularly when friction mating is used as the sealing mechanism.

The syringe may be constructed of a wide range of materials including plastics, metal, glass and the like, although injection moldable plastics are preferred. The barrel, plunger and pressure pad are conveniently molded of a polyolefin, such as polyethylene or polypropylene, while the cannula is molded of a more flexible and soft thermoplastic material such as polyvinylchloride, although lower molecular weight polyolefins, such as polyethylene and polypropylene may be used in this regard. The cannula cap may be conveniently produced from any thermoplastic polymer, but again a polyolefin or polyvinylchloride is preferred. The techniques of molding and producing syringe barrels and pistons of this nature are well known in the art and need not be described herein.

Suitable enema fluid for use in the present syringe will be a water solution of a lubricant, e.g., dioctyl sodium sulfosuccinate, USP, 250 mg., and glycerine, USP, optionally with sorbic acid as a preservative. The syringe barrel is suitably about 7.5 cm long by 2 cm in diameter to provide a enema fluid cavity containing about 12 ml of enema fluid. The cannula is about 5 cm long with a maximum length of about 7 cm.

What is claimed is:

1. A disposable enema syringe for self-application and/or one hand use comprising:
   (a) a barrel with a bore therein, said barrel having an open end with a transversely extending flange at least partially disposed about the open end and the barrel having a discharge end with a discharge orifice therein;
   (b) a movable piston disposed within the bore whereby an enema fluid receiving cavity in the bore is defined by the space between the piston and the discharge end of the barrel;
   (c) a plunger having one end operably connected to the piston and the other end extending out of the bore and terminating in a digit receiving pressure pad, the said pressure pad being at a distance from the said flange which is at least substantially equal to the distance of the said cavity between the piston and discharge end, and wherein the distance from the said flange to the said pressure pad being such that the syringe may be controllably grasped by one hand between the thumb and a finger around the barrel and next to the flange and the index or second finger on the said pressure pad;
   (d) a cannula made of a soft and flexible thermoplastic material, having one end thereof directly connected to and retained in the discharge orifice of said barrel to provide a fluid seal between the cannula and the barrel and to provide fluid communication with said discharge orifice, and the other end having a cannula orifice, said cannula having a decreasing taper commencing from the end thereof connected to the discharge orifice of the barrel and ending with the cannula orifice, said cannula being sufficiently long that it may be inserted into the rectum with only one hand;
   whereby the cannula may be inserted into the rectum and the enema fluid injected from the syringe into the rectum with the use of only one hand.

2. The syringe of claim 1 wherein the cannula is constructed of a material which is substantially more flexible than the material of which said barrel is constructed.

3. The syringe of claim 1 wherein a removable cannula cap extends over at least the cannula orifice.

4. The syringe of claim 3 wherein the cannula cap extends over at least that portion of the cannula which will be inserted into the rectum of the user when the syringe is in use.

5. The syringe of claim 1 wherein the said friction mating is at a portion of the cannula which will not be inserted into the rectum of the user when the syringe is in use.

6. The syringe of claim 1 wherein the said tapers form an annulus between the cap and the cannula.

7. The syringe of claim 6 wherein enema fluid in the said cavity may flow into said annulus and provide a self-lubricating cannula.

8. The syringe of claim 4 wherein the cannula cap has a corresponding taper but which taper terminates at a distance where the cannula cap will form a friction mating between the inside surface of the cannula cap and the outside surface of the cannula.

* * * * *